US012599504B2

(12) United States Patent
Pratt et al.

(10) Patent No.: US 12,599,504 B2
(45) Date of Patent: Apr. 14, 2026

(54) WOUND DRESSING WITH FLUID MANAGEMENT

(71) Applicant: Solventum Intellectual Properties Company, Maplewood, MN (US)

(72) Inventors: Benjamin A. Pratt, Wimborne (GB); David R. Mercer, San Antonio, TX (US); Colin J. Hall, Wimborne (GB)

(73) Assignee: Solventum Intellectual Properties Company, Maplewood, MN (US)

( * ) Notice: Subject to any disclaimer, the term of this patent is extended or adjusted under 35 U.S.C. 154(b) by 1037 days.

(21) Appl. No.: 17/294,580

(22) PCT Filed: Nov. 19, 2019

(86) PCT No.: PCT/US2019/062119
§ 371 (c)(1),
(2) Date: May 17, 2021

(87) PCT Pub. No.: WO2020/106672
PCT Pub. Date: May 28, 2020

(65) Prior Publication Data
US 2021/0393442 A1 Dec. 23, 2021

Related U.S. Application Data

(60) Provisional application No. 62/770,333, filed on Nov. 21, 2018.

(51) Int. Cl.
*A61F 13/05* (2024.01)
*A61F 13/02* (2024.01)
(Continued)

(52) U.S. Cl.
CPC .......... *A61F 13/05* (2024.01); *A61F 13/0209* (2013.01); *A61F 13/0223* (2013.01);
(Continued)

(58) Field of Classification Search
CPC .. A61F 13/05; A61F 13/0209; A61F 13/0223; A61F 13/0226; A61F 13/0259; A61F 13/0236; A61F 13/024
See application file for complete search history.

(56) References Cited

U.S. PATENT DOCUMENTS 1,355,846 A 10/1920 Rannells
2,547,758 A 4/1951 Keeling
(Continued)

FOREIGN PATENT DOCUMENTS

AU 650575 B2 3/1986
AU 745271 B2 3/2002
(Continued)

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.
(Continued)

*Primary Examiner* — Jessica Arble

(57) ABSTRACT

A dressing includes an evaporative film layer having a wound-facing side and a non-wound¬ facing side. The evaporative film layer has a high moisture vapor transfer rate. The dressing includes a carrier film layer coupled to the non-wound-facing side of the evaporative film layer. A plurality of holes extends through the carrier film layer. The dressing includes a superab sorbent layer coupled to the wound-facing side of the evaporative film layer and a wicking layer coupled to the superab sorbent layer. The superab sorbent layer is positioned between the wicking layer and the evaporative film layer. The wicking layer is configured to wick fluid from a wound, the superab sorbent layer is configured to absorb fluid from the wicking layer, and the evaporative film layer and the carrier film layer (Continued)

allow evaporation of fluid from the superabsorbent layer through the holes. The carrier film layer provides structural support to the evaporative film layer.

13 Claims, 3 Drawing Sheets

(51) Int. Cl.

| | |
|---|---|
| *A61F 13/0203* | (2024.01) |
| *A61F 13/0206* | (2024.01) |
| *A61L 26/00* | (2006.01) |
| *A61M 1/00* | (2006.01) |

(52) U.S. Cl.
CPC ...... *A61F 13/0226* (2013.01); *A61F 13/0259* (2013.01); *A61F 13/0289* (2013.01); *A61L 26/008* (2013.01); *A61M 1/913* (2021.05); *A61M 1/915* (2021.05); *A61M 1/962* (2021.05); *A61M 1/985* (2021.05); *A61F 13/0236* (2013.01); *A61F 13/024* (2013.01)

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,060,662 A * | 10/1991 | Farnswoth, III | A61F 15/008 |
| | | | 128/894 |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 5,891,077 A * | 4/1999 | Gilman | A61F 13/025 |
| | | | 602/44 |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2009/0227969 A1 | 9/2009 | Jaeb et al. | |
| 2011/0028918 A1* | 2/2011 | Hartwell | A61F 13/022 |
| | | | 604/319 |
| 2011/0054421 A1* | 3/2011 | Hartwell | A61M 1/985 |
| | | | 604/319 |
| 2011/0257572 A1 | 10/2011 | Locke et al. | |
| 2014/0031771 A1* | 1/2014 | Locke | A61M 1/985 |
| | | | 156/60 |
| 2014/0228786 A1* | 8/2014 | Croizat | A61M 1/915 |
| | | | 604/319 |
| 2015/0245950 A1* | 9/2015 | Locke | A61M 1/915 |
| | | | 604/319 |
| 2017/0135862 A1* | 5/2017 | Tuck | A61M 1/90 |
| 2017/0326004 A1* | 11/2017 | Long | A61F 13/00063 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |

(56)                    References Cited

FOREIGN PATENT DOCUMENTS

| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| EP | 2 558 045 A1 | 2/2013 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Bjorn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

(56) References Cited

OTHER PUBLICATIONS

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians; Jul. 2007.

International Search Report and Written Opinion on International Patent Application No. PCT/US2019/062119 dated Feb. 21, 2020 (9 pages).

* cited by examiner

WOUND DRESSING WITH FLUID MANAGEMENT

CROSS-REFERENCE TO RELATED APPLICATIONS

The present application is a US national phase application under 35 USC § 371 of International Application No. PCT/US2019/062119 filed on Nov. 19, 2019. which claims the benefit of priority to U.S. Provisional Application No. 62/770,333, entitled "Wound Dressing With Fluid Management" filed on Nov. 21, 2018, which are hereby incorporated herein by reference in their entireties.

BACKGROUND

The present disclosure relates generally to the field of dressing for wounds, and in particular to dressings configured to handle fluid exuded from a wound. Such dressings may be configured to absorb fluid from the wound, store the fluid, and/or allow the fluid to be removed from the dressing. One challenge faced by such dressings is providing a proper level of fluid absorption that prevents maceration caused by fluid pooling at the wound or periwound while also preventing a wound from being dried more than may be preferable for wound healing. Another challenge faced by such dressings is providing fluid handling with materials which are durable in use and easy to manufacture.

SUMMARY

One implementation of the present disclosure is a dressing. The dressing includes an evaporative film layer having a wound-facing side and a non-wound-facing side. The evaporative film layer has a high moisture vapor transfer rate. The dressing also includes a carrier film layer coupled to the non-wound-facing side of the evaporative film layer. A plurality of holes extends through the carrier film layer. The dressing also includes a superabsorbent layer coupled to the wound-facing side of the evaporative film layer and a wicking layer coupled to the superabsorbent layer. The superabsorbent layer is positioned between the wicking layer and the evaporative film layer. The wicking layer is configured to wick fluid from a wound, the superabsorbent layer is configured to absorb the fluid from the wicking layer, and the evaporative film layer and the carrier film layer allow evaporation of the fluid from the superabsorbent layer through the plurality of holes. The carrier film layer provides structural support to the evaporative film layer.

In some embodiments, the dressing also includes a support film layer removably coupled to the evaporative film layer and a release liner removably coupled to the support film layer. The wicking layer, the superabsorbent layer, the evaporative film layer, and the carrier film layer are positioned between the release liner and the support film layer. The support film layer and the release liner are removable from the dressing to prepare the dressing for application to a wound.

In some embodiments, the support film layer includes a plurality of second holes. The plurality of second holes is aligned with the plurality of holes. In some embodiments, the support film layer facilitates creation of the plurality of holes by providing structural support to the carrier film layer during manufacturing.

In some embodiments, the plurality of holes is arranged in a plurality of adjacent parallel rows extending longitudinally along the dressing. Each parallel row includes a subset of the plurality of holes. In some embodiments, the adjacent parallel rows are spaced laterally apart from one another. A first row of the adjacent parallel rows is shifted longitudinally relative to a second row of the adjacent parallel rows.

In some embodiments, the dressing includes a wound contact layer coupled to the wicking layer. The wound contact layer includes at least one of hydrogel or hydrocolloid.

In some embodiments, the dressing includes a fenestrated film layer positioned between the superabsorbent layer and the wicking layer. The fenestrated film layer is configured to allow the fluid to flow from the wicking layer to the superabsorbent layer and partially prevent the fluid from flowing from the superabsorbent layer to the wicking layer. In some embodiments, the fenestrated film layer is configured to restrict a rate of fluid flow from the wicking layer to the superabsorbent layer.

In some embodiments, the dressing includes a reduced-pressure interface coupled to the carrier film layer and a channel aligned with the reduced-pressure interface and extending through the carrier film layer and the evaporative film layer. In some embodiments, the reduced-pressure interface and the channel are configured to facilitate fluid communication between the wicking layer and a pump. The pump is configured to draw a negative pressure at the absorbent layer. In some embodiments, the dressing includes a manifold layer positioned between the evaporative film layer and the superabsorbent layer.

Another implementation of the present disclosure is a wound therapy system. The wound therapy system includes a pump, a tube fluidly communicable with the pump, and a dressing coupleable to the tube. The dressing includes an evaporative film layer having a wound-facing side and a non-wound-facing side. The evaporative film layer has a high moisture vapor transfer rate. The dressing also includes a carrier film layer coupled to the non-wound-facing side of the evaporative film layer and including a plurality of holes extending through the carrier film layer, a superabsorbent layer coupled to the wound-facing side of the evaporative film layer, and a wicking layer coupled to the superabsorbent layer. The superabsorbent layer is positioned between the wicking layer and the evaporative film layer. The wicking layer is configured to wick fluid from a wound, the superabsorbent layer is configured to absorb the fluid from the absorbent layer, and the evaporative film layer and the carrier film layer allow evaporation of the fluid from the superabsorbent layer through the plurality of holes. The carrier film layer provides structural support to the evaporative film layer. The tube is fluidly communicable with the wicking layer and the pump is configured to draw a negative pressure at the wicking layer via the tube.

In some embodiments, the wound therapy system includes a reduced-pressure interface coupled to the carrier film layer and a channel extending through the evaporative film layer and the carrier film layer. The reduced-pressure interface is coupleable to the tube such that the tube is in fluid communication with the superabsorbent layer and the wicking layer via the channel. In some embodiments, the reduced-pressure interface includes a filter that allows air to flow from the dressing to the tube and substantially prevents the fluid from flowing from the dressing to the tube.

In some embodiments, the support film layer includes a plurality of second holes. The plurality of second holes is aligned with the plurality of holes. In some embodiments, the support film layer facilitates creation of the plurality of holes by providing structural support to the carrier film layer during manufacturing.

In some embodiments, the wound therapy system includes a manifold layer positioned between the evaporative film layer and the superabsorbent layer.

In some embodiments, the plurality of holes is aligned with the superabsorbent layer. In some embodiments, the plurality of holes is arranged in a plurality of adjacent parallel rows extending longitudinally along the dressing. Each parallel row includes a subset of the plurality of holes. In some embodiments, the adjacent parallel rows are spaced laterally apart from one another. A first row of the adjacent parallel rows is shifted longitudinally relative to a second row of the adjacent parallel rows.

In some embodiments, the wound therapy system includes a wound contact layer coupled to the wicking layer. The wound contact layer includes at least one of a perforated polyurethane film or a woven polyester fabric.

Another implementation of the present disclosure is a method of manufacturing a dressing. The method includes adhering a carrier film layer to a support layer, creating a plurality of holes through the carrier film layer and the support layer, and coupling the carrier film layer to a non-wound-facing side of an evaporative film layer. The evaporative film layer has a high moisture vapor transfer rate. The method also includes coupling a superabsorbent layer to a wound-facing side of the evaporative film layer, coupling a wicking layer to the superabsorbent layer, and coupling a release liner to the support layer such that the carrier film layer, the superabsorbent layer, and the wicking layer are positioned between the release liner and the support layer. The release liner and the support layer are removable from the carrier film layer, the superabsorbent layer, and the wicking layer.

In some embodiments, the wicking layer is configured to wick fluid from a wound. The superabsorbent layer is configured to absorb the fluid from the absorbent layer. The evaporative film layer and the carrier film layer allow evaporation of the fluid from the superabsorbent layer through the plurality of holes. The carrier film layer provides structural support to the evaporative film layer.

In some embodiments, adhering a carrier film layer to a support layer includes providing, with the support layer, structural support to the carrier film layer that facilitates creation of the plurality of holes through the carrier film layer. In some embodiments, the method includes aligning the plurality of holes with the superabsorbent layer.

In some embodiments, creating the plurality of holes through the carrier film layer and the support layer includes creating a plurality of parallel rows extending longitudinally along the support layer and the carrier film layer. Each parallel row includes a subset of the plurality of holes.

In some embodiments, the method includes coupling a wound contact layer to the wicking layer. The wound contact layer includes at least one of hydrogel or hydrocolloid. In some embodiments, the method includes positioning a fenestrated film layer between the wicking layer and the superabsorbent layer.

In some embodiments, the method includes creating a channel through the carrier film layer and the evaporative film layer and coupling a reduced-pressure interface to the carrier film layer in fluid communication with the channel.

In some embodiments, the method includes placing a pump in fluid communication with the wicking layer via the channel, the reduced-pressure interface, and a tube. The pump is configured to draw a negative pressure at the dressing. In some embodiments, the method includes positioning a manifold layer between the evaporative film layer and the superabsorbent layer.

DETAILED DESCRIPTION

Figure 1:
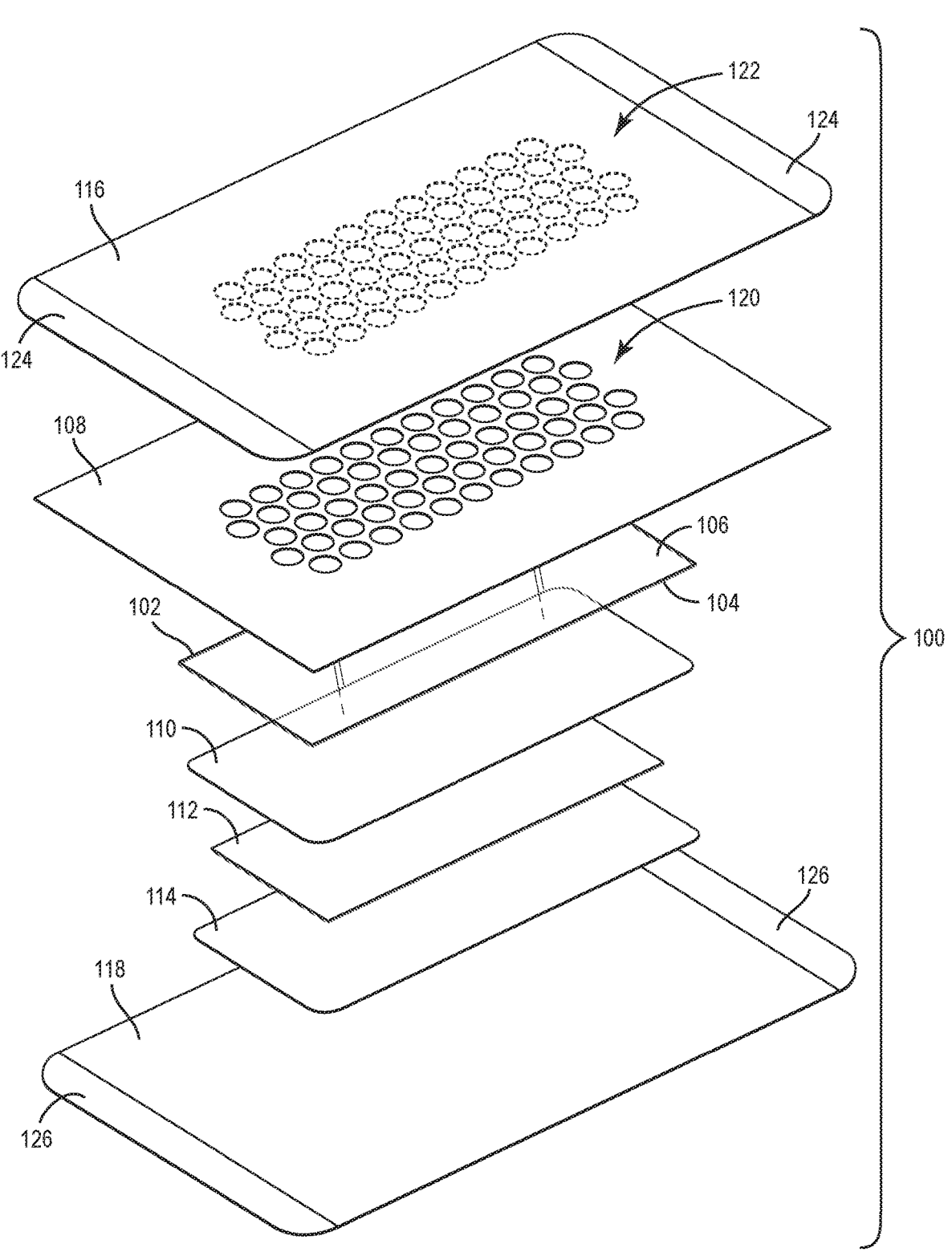
FIG. 1 is an exploded view of a dressing, according to a first exemplary embodiment.

Referring to FIG. 1, a dressing 100 is shown, according to a first exemplary embodiment. The dressing 100 includes an evaporative film layer 102 having a wound-facing side 104 and a non-wound-facing side 106, a carrier film layer 108 coupled to the non-wound-facing side 106 of the evaporative film layer 102, a superabsorbent layer 110 coupled to the wound-facing side 104 of the evaporative film layer 102, and a wicking layer 112 coupled to the superabsorbent layer 110. The dressing 100 is shown to include a wound contact layer 114 coupled to the wicking layer 112. The dressing 100 is also shown to include a support film layer 116 coupled to the carrier film layer 108 and a release liner 118 coupled to the support film layer 116 such that the wound contact layer 114, the wicking layer 112, the superabsorbent layer 110, the evaporative film layer 102, and the carrier film layer 108 are positioned between the support film layer 116 and the release liner 118.

The wound contact layer 114 is configured to be placed abutting a wound. The wound contact layer 114 may be configured to substantially prevent adherence of the dressing 100 to the wound. The wound contact layer 114 may allow fluid exuded from the wound to flow therethrough. In various embodiments, the wound contact layer 114 includes one or more of silicone, a polyurethane film, or a woven polyester fabric. In some embodiments, the wound contact layer 114 is perforated or fenestrated. In some embodiments, the wound contact layer 114 includes a hydrocolloid or hydrogel, which may provide comfort and provide moisture to dry wounds.

The wicking layer 112 is configured to wick fluid from the wound (e.g., via the wound contact layer 114) to the superabsorbent layer 110. The wicking layer 112 may include a hydrophilic foam, a non-woven dry polyester textile, or some other material capable of wicking fluid. The wicking layer 112 may allow air to flow therethrough, for example to allow a negative pressure to be distributed across a wound. The wicking layer 112 may include a less-capable absorbent as compared to the superabsorbent layer 110, which may provide a gradient that causes fluid to flow away from the wound. The wicking layer 112 may also provide reverse transfer of fluid from the superabsorbent layer 110 to the wicking layer 112 and towards the wound in a scenario where the wound becomes drier than a preferable level (e.g., when a wound-facing side of the wicking layer 112 is drier than an opposing side of the wicking layer 112 proximate the superabsorbent layer 110).

The superabsorbent layer 110 is configured to absorb fluid from the wicking layer 112, retain the fluid, and allow the fluid to evaporate to the environment via the evaporative film layer 102. In some embodiments, the superabsorbent layer 110 includes a sheet or pouch of superabsorbent material. In some embodiments, the superabsorbent layer 110 includes multiple superabsorbent deposits printed on the wicking layer 112, for example arranged in a pattern on the wicking layer 112. In some embodiments, the superabsorbent layer 110 includes a superabsorbent laminate, for example as described in U.S. Patent Application No. 62/788, 036 filed on Jan. 3, 2019, incorporated by reference herein in its entirety.

The evaporative film layer 102 is made of a high moisture vapor transfer rate (MVTR) film, for example a high-MVTR polyurethane film. The evaporative film layer 102 thereby facilitates evaporation of fluid through the evaporative film layer 102, for example from the superabsorbent layer 110 to the environment. In preferred embodiments, the evaporative film layer 102 abuts the superabsorbent layer 110 without an adhesive or other obstruction between the superabsorbent layer 110 and the evaporative film layer 102.

The carrier film layer 108 is coupled to the evaporative film layer 102 and configured to provide structural support to the evaporative film layer 102. High MVTR materials are often thinner and more fragile than may be preferable for providing a robust, durable, and long-lasting external surface of a dressing. The carrier film layer 108 may be made of a thicker and/or more durable material than the evaporative film layer 102, such that the carrier film layer 108 may protect the evaporative film layer 102.

To allow evaporation therethrough, the carrier film layer 108 includes a plurality of holes 120 extending through the carrier film layer 108. The holes 120 are aligned with the evaporative film layer 102 and the superabsorbent layer 110. In the embodiment shown in FIG. 1, the holes 120 are arranged in multiple adjacent parallel rows that extend longitudinally along the dressing 100, with each of the parallel rows including a subset of the multiple holes 120. The adjacent parallel rows are space laterally apart from one another, which each row shifted longitudinally relative to a neighboring row. That is, in the example shown, an equilateral triangle is formed by two holes 120 from a first row and one hole 120 from a neighboring row. Such an arrangement may expose a large portion of the surface area of the evaporative film layer 102 to the environment while also providing structure and support distributed throughout the exposed area. Various other patterns of holes 120 may be included in various embodiments.

The support film layer 116 is configured to provide support for the carrier film layer 108 and act as packaging for the dressing 100, for example to facilitate a user in manipulating and positioning the dressing 100. The support film layer 116 is removably coupled (i.e., removable from) the carrier film layer 108. Accordingly, the support film layer 116 may be optionally removed from the dressing 100 when the dressing 100 is deployed to treat a wound. The support film layer 116 may be made of a polyurethane drape material. The support film layer 116 includes support bars (handling bars) 124 that further facilitate handling of the dressing 100. The support bars 124 may have a higher rigidity than other portions of the dressing 100.

As shown in FIG. 1, the support film layer 116 includes multiple holes 122. The holes 122 in the support film layer 116 align with the holes 120 in the carrier film layer 108. To manufacture the support film layer 116 and the carrier film layer 108, the carrier film layer 108 may be coupled (e.g., adhered) to the support film layer 116, and then the holes 122 and holes 120 may be simultaneous created (e.g., cut) in both the support film layer 116 and the carrier film layer 108. The support film layer 116 may thereby facilitate creation of the holes 120 in the carrier film layer 108, particularly in cases where cutting or otherwise creating the holes 120 in the carrier film layer 108 alone may be difficult or unreliable due to the thinness, flexibility, or other characteristic of the carrier film layer 108. In other embodiments, the support film layer 116 does not have holes extending therethrough.

The release liner 118 is removably coupled to the support film layer 116, such that the wound contact layer 114, the wicking layer 112, the superabsorbent layer 110, the evaporative film layer 102, and the carrier film layer 108 are positioned between the support film layer 116 and the release liner 118. The release liner 118 and the support film layer 116 may combine to substantially prevent contaminants from entering the dressing 100 before the dressing 100 is deployed to treat a wound. The release liner 118 includes support bars (handling bars) 126 configured to facilitate handling of the release liner 118 and the dressing 100. The support bars 126 of the release liner 118 may be aligned with the support bars 124 of the support film layer 116.

Figure 2:
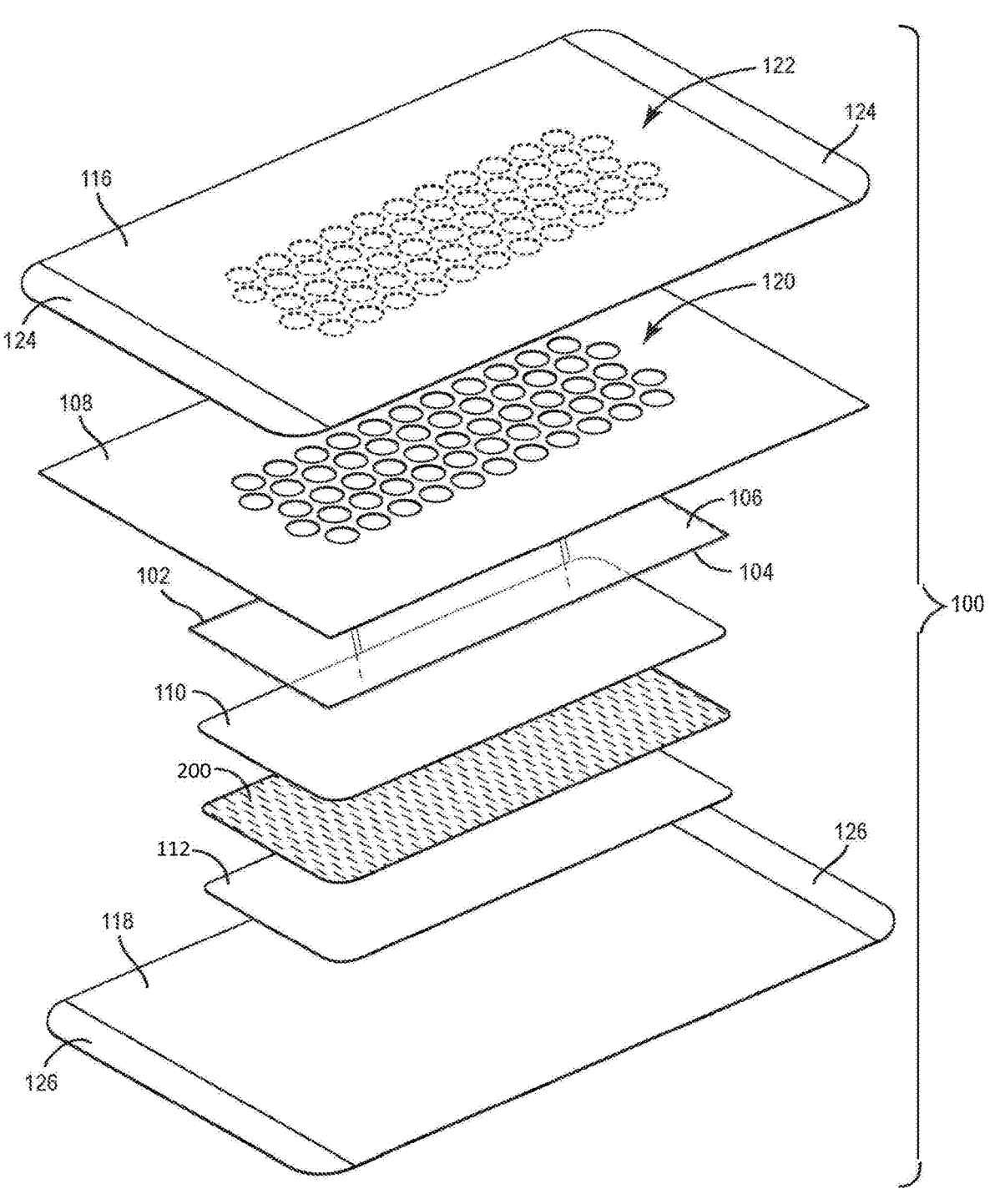
FIG. 2 is an exploded view of a dressing, according to a second exemplary embodiment.

Referring now to FIG. 2, an exploded view of a second embodiment of the dressing 100 is shown, according to an exemplary embodiment. As in FIG. 1, the dressing 100 as shown in FIG. 2 includes the evaporative film layer 102, the carrier film layer 108, the superabsorbent layer 110, the wicking layer 112, the support film layer 116, and the release liner 118. As shown in FIG. 2, the dressing 100 also includes a fenestrated film layer 200 positioned between the wicking layer 112 and the superabsorbent layer 110.

The fenestrated film layer 200 is configured to manage a rate of fluid flow between the wicking layer 112 and the superabsorbent layer 110. The fenestrated film layer 200 may restrict fluid from flowing from the superabsorbent layer 110 towards the wound and periwound (i.e., towards the wicking layer 112), which may reduce the risk of maceration. In some embodiments, the fenestrated film layer 200 may limit the rate at which fluid flows from the wicking layer 112 to the superabsorbent layer 110, for example to reduce the risk of a wound becoming drier than may be preferable for wound healing. The materials and fenestration size and density of the fenestrated film layer 200 may be chosen to optimize the rate and direction of fluid flow between the wicking layer 112 and the superabsorbent layer 110.

Also as shown in FIG. 2, in some embodiments the wound contact layer 114 may be omitted. In such a case, the wicking layer 112 may be configured to contact a wound. A hydrogel or hydrocolloid may be included. In other embodiments of the dressing 100 of FIG. 2, the wound contact layer 114 may be included while the wicking layer 112 is omitted. In some embodiments, the wound contact layer 114, the wicking layer 112, and the fenestrated film layer 200 are all included.

Figure 3:
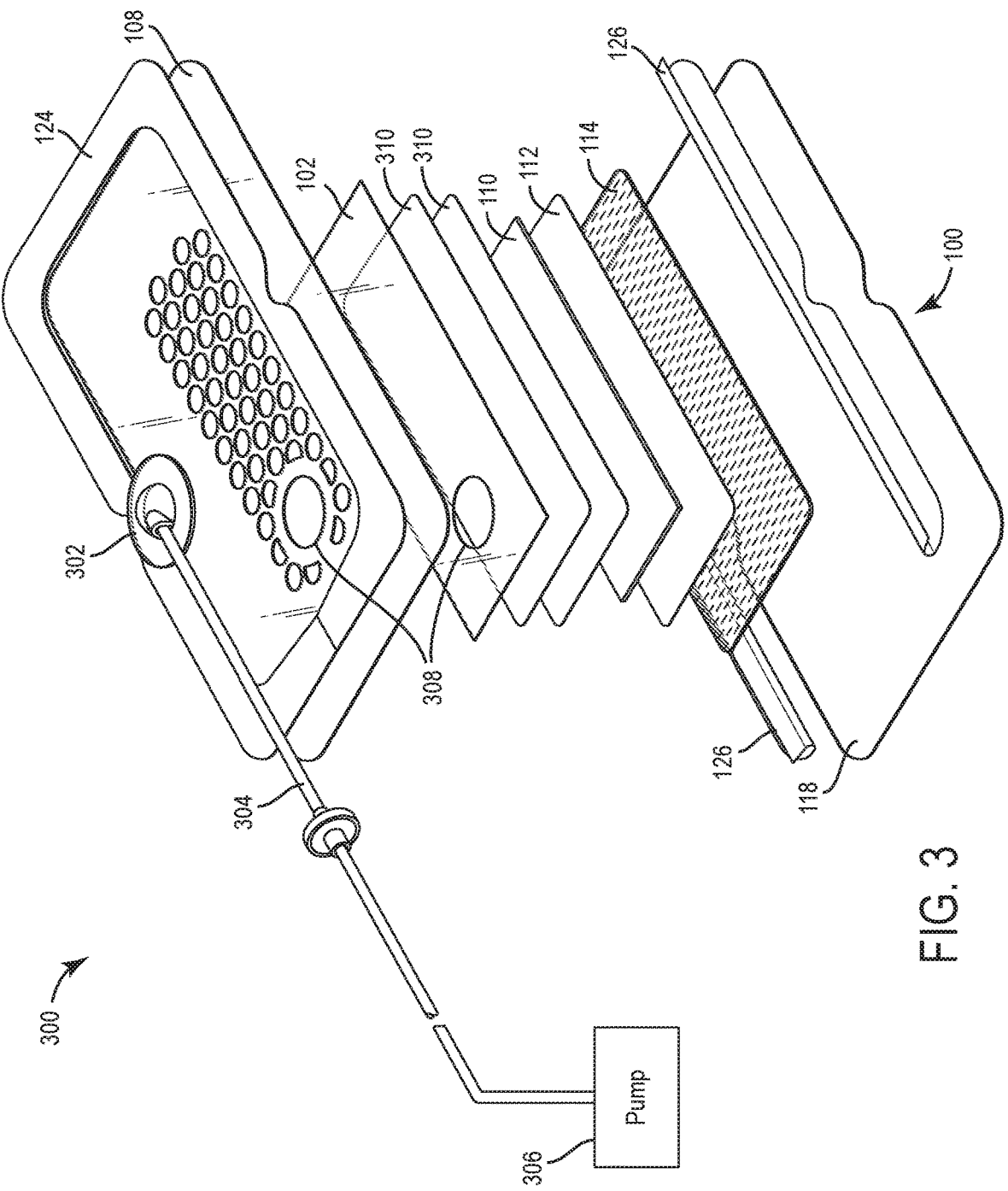
FIG. 3 is an exploded view of a negative pressure wound therapy system, according to an exemplary embodiment.

Referring now to FIG. 3, a negative pressure wound therapy system 300 is shown, according to an exemplary embodiment. The negative pressure wound therapy system 300 includes the dressing 100, a connection pad (reduced-pressure interface) 302 coupled to the dressing 100 (e.g., coupled to the carrier film layer 108), a tube 304 coupled to the connection pad 302, and a pump 306 coupled to the tube 304.

FIG. 3 shows a third embodiment of the dressing 100 which is suitable for use in applying negative pressure (i.e., reduced pressure relative to atmospheric pressure) to a wound. The dressing 100 includes the evaporative film layer 102, the carrier film layer 108, the superabsorbent layer 110, the wicking layer 112, the wound contact layer 114, and the release liner 118. The dressing 100 is shown to include the support bars 124 of the support film layer 116 and the support bars 126 of the release liner 118, which may add stability and support to the dressing 100 and/or allow the dressing 100 to be sealed over a wound.

As shown in FIG. 3, the dressing 100 also includes two manifold layers 310. In various embodiments, one or more manifold layers 310 may be included. The manifold layers 310 are configured to allow air to flow therethrough to facilitate the distribution of pressure substantially uniformly across the dressing 100. The manifold layers 310 may be made of a non-woven dry polyester textile. The manifold layers 310 may also be configured to wick fluid from the superabsorbent layer 110 to the evaporative film layer 102 to allow the fluid to evaporate via the holes 120 in the carrier film layer 108.

The superabsorbent layer 110 and/or the wicking layer 112 may also be configured to allow air to flow therethrough, thereby facilitating the distribution of negative pressure through the superabsorbent layer 110 and/or the wicking layer 112. The wound contact layer 114 may be fenestrated (perforated, covered with a pattern of holes, etc.) to allow the communication of negative pressure from the dressing 100 to the wound.

As shown in FIG. 3, the dressing 100 also includes a channel 308 extending through the carrier film layer 108 and the evaporative film layer 102 to the manifold layers 310. In the embodiment shown, the channel 308 is surrounded by holes 120 in the carrier film layer 108. The holes 120 may be spaced apart from the channel 308.

The connection pad 302 is aligned with the channel 308, placing the connection pad 302, the tube 304, and the pump 306 in pneumatic communication with the manifold layers 310 via the channel 308 (i.e., so that air can flow substantially freely between the manifold layers 310 and the pump 306). The pump 306 is configured to draw air out of the dressing 100 to create a negative pressure at the dressing 100 (i.e., at the manifold layers 310, the superabsorbent layer 110, the wicking layer 112) and at the wound. In various embodiments, the pump 306 may be a battery-powered portable device, a mechanically-powered portable device, or may be included in an electrically-powered wound therapy unit. In some embodiments, the pump 306 is configured to remove fluid and debris from the dressing 100 via the tube 304.

In some embodiments a hydrophobic filter is included in the connection pad 302 and substantially prevents fluid or debris from entering the tube 304. In such a case, fluid is absorbed by the superabsorbent layer 110 and evaporates through the evaporative film layer 102 and the holes 120 in the carrier film layer 108, while air is removed from the dressing 100 by the pump 306.

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the disclosure as recited in the appended claims.

It should be noted that the term "exemplary" and variations thereof, as used herein to describe various embodiments, are intended to indicate that such embodiments are possible examples, representations, or illustrations of possible embodiments (and such terms are not intended to connote that such embodiments are necessarily extraordinary or superlative examples).

The term "coupled" and variations thereof, as used herein, means the joining of two members directly or indirectly to one another. Such joining may be stationary (e.g., permanent or fixed) or moveable (e.g., removable or releasable). Such joining may be achieved with the two members coupled directly to each other, with the two members coupled to each other using a separate intervening member and any additional intermediate members coupled with one another, or with the two members coupled to each other using an intervening member that is integrally formed as a single unitary body with one of the two members. If "coupled" or variations thereof are modified by an additional term (e.g., directly coupled), the generic definition of "coupled" provided above is modified by the plain language meaning of the additional term (e.g., "directly coupled" means the joining of two members without any separate intervening member), resulting in a narrower definition than the generic definition of "coupled" provided above. Such coupling may be mechanical, electrical, or fluidic.

References herein to the positions of elements (e.g., "top," "bottom," "above," "below") are merely used to describe the orientation of various elements in the FIGURES. It should be noted that the orientation of various elements may differ according to other exemplary embodiments, and that such variations are intended to be encompassed by the present disclosure.

Although the figures and description may illustrate a specific order of method steps, the order of such steps may differ from what is depicted and described, unless specified differently above. Also, two or more steps may be performed concurrently or with partial concurrence, unless specified differently above. All such variations are within the scope of the disclosure.

What is claimed is:

1. A dressing, comprising:
an evaporative film layer comprising a wound-facing side and a non-wound-facing side, the evaporative film layer configured to transfer moisture vapor;
a carrier film layer coupled to the non-wound-facing side of the evaporative film layer and comprising a plurality of holes extending through the carrier film layer;
a superabsorbent layer in direct contact with the wound-facing side of the evaporative film layer;
a wicking layer coupled in direct fluid communication to the superabsorbent layer, the superabsorbent layer positioned between the wicking layer and the evaporative film layer; and
an opening disposed through the evaporative film layer and configured to provide fluid communication therethrough, wherein the opening is defined by a removed portion of a substrate material of the evaporative film layer;
wherein:
the wicking layer is configured to wick fluid from a wound;
the superabsorbent layer is configured to absorb the fluid from the wicking layer; and
the evaporative film layer and the carrier film layer allow evaporation of the fluid from the superabsorbent layer through the plurality of holes, the carrier film layer providing structural support to the evaporative film layer.

2. The dressing of claim 1, comprising:
a support film layer removably coupled to the evaporative film layer; and
a release liner removably coupled to the support film layer;

wherein the wicking layer, the superabsorbent layer, the evaporative film layer, and the carrier film layer are positioned between the release liner and the support film layer; and wherein the support film layer and the release liner are removable from the dressing to prepare the dressing for application to a wound.

3. The dressing of claim 2, wherein the support film layer comprises a plurality of second holes, the plurality of second holes aligned with the plurality of holes and wherein the support film layer facilitates creation of the plurality of holes by providing structural support to the carrier layer during manufacturing.

4. The dressing of claim 1, wherein the plurality of holes are aligned with the superabsorbent layer.

5. The dressing of claim 1, wherein the plurality of holes are arranged in a plurality of adjacent parallel rows extending longitudinally along the dressing, each parallel row comprising a subset of the plurality of holes and wherein the adjacent parallel rows are spaced laterally apart from one another; and wherein a first row of the adjacent parallel rows is shifted longitudinally relative to a second row of the adjacent parallel rows.

6. The dressing of claim 1, comprising a wound contact layer coupled to the wicking layer, the wound contact layer comprising at least one of hydrogel or hydrocolloid.

7. The dressing of claim 1, comprising a fenestrated film layer positioned between the superabsorbent layer and the wicking layer, the fenestrated film layer configured to allow the fluid to flow directly from the wicking layer to the superabsorbent layer and partially prevent the fluid from flowing from the superabsorbent layer to the wicking layer, and wherein the fenestrated film layer is configured to restrict a rate of fluid flow from the wicking layer to the superabsorbent layer.

8. The dressing of claim 1, comprising:
a reduced-pressure interface coupled to the carrier film layer; and
a channel aligned with the reduced-pressure interface and extending through the carrier film layer and the opening in the evaporative film layer;
a manifold layer positioned between the evaporative film layer and the superabsorbent layer;
wherein the reduced-pressure interface and the channel are configured to facilitate fluid communication between the wicking layer and a pump, the pump configured to draw a negative pressure at the superabsorbent layer.

9. A wound therapy system, comprising:
a pump;
a tube fluidly communicable with the pump; and
a dressing coupleable to the tube, the dressing comprising:
an evaporative film layer comprising a wound-facing side and a non-wound facing side, the evaporative film layer configured to transfer moisture vapor;
a carrier film layer coupled to the non-wound-facing side of the evaporative film layer and comprising a plurality of holes extending through the carrier film layer;

a superabsorbent layer directly abutting the wound-facing side of the evaporative film layer without an adhesive between the superabsorbent layer and the evaporative film layer;
a wicking layer coupled in direct fluid communication to the superabsorbent layer, the superabsorbent layer positioned between the wicking layer and the evaporative film layer;
an opening disposed through the evaporative film layer and configured to provide fluid communication therethrough, wherein the opening is defined by a removed portion of a substrate material of the evaporative film layer;
wherein:
the wicking layer is configured to wick fluid from a wound;
the superabsorbent layer is configured to absorb the fluid from the wicking layer;
the evaporative film layer and the carrier film layer allow evaporation of the fluid from the superabsorbent layer through the plurality of holes, the carrier film layer providing structural support to the evaporative film layer;
the tube is fluidly communicable with the wicking layer and the pump is configured to draw a negative pressure at the wicking layer via the tube.

10. The wound therapy system of claim 9, comprising:
a reduced-pressure interface coupled to the carrier film layer; and
a channel extending through the opening in the evaporative film layer and the carrier film layer;
wherein the reduced-pressure interface is coupleable to the tube such that the tube is in fluid communication with the superabsorbent layer and the wicking layer via the channel, and wherein the reduced-pressure interface comprises a filter that allows air to flow from the dressing to the tube and substantially prevents the fluid from flowing from the dressing to the tube.

11. The wound therapy system of claim 9, comprising:
a support film layer removably coupled to the evaporative film layer; and
a release liner removably coupled to the support film layer;
wherein the wicking layer, the superabsorbent layer, the evaporative film layer, and the carrier film layer are positioned between the release liner and the support film layer; and
wherein the support film layer and the release liner are removable from the dressing to allow application of the dressing to a wound.

12. The wound therapy system of claim 11, wherein the support film layer comprises a plurality of second holes, the plurality of second holes aligned with the plurality of holes, and wherein the support film layer facilitates creation of the plurality of holes providing structural support to the carrier film layer during manufacturing.

13. The wound therapy system of claim 9, comprising a wound contact layer coupled to the wicking layer, the wound contact layer comprising at least one of a perforated polyurethane film or a woven polyester fabric.

* * * * *